United States Patent
Jamison et al.

(10) Patent No.: US 11,360,014 B1
(45) Date of Patent: Jun. 14, 2022

(54) METHODS AND SYSTEMS FOR CHARACTERIZING FLUID COMPOSITION AND PROCESS OPTIMIZATION IN INDUSTRIAL WATER OPERATIONS USING MEMS TECHNOLOGY

(71) Applicant: Halliburton Energy Services, Inc., Houston, TX (US)

(72) Inventors: Dale E. Jamison, Humble, TX (US); William Walter Shumway, Spring, TX (US); Preston Andrew May, Porter, TX (US); Jay Paul Deville, Spring, TX (US); Troy Francis Davis, Baton Rouge, LA (US); Frederick Thomas Brown, Naperville, IL (US)

(73) Assignee: Multi-Chem Group, LLC, Houston, TX (US)

( * ) Notice: Subject to any disclaimer, the term of this patent is extended or adjusted under 35 U.S.C. 154(b) by 0 days.

(21) Appl. No.: 17/379,858

(22) Filed: Jul. 19, 2021

(51) Int. Cl.
*G01N 15/06* (2006.01)
*B81B 3/00* (2006.01)
(Continued)

(52) U.S. Cl.
CPC .......... *G01N 15/06* (2013.01); *B81B 3/0062* (2013.01); *G01N 29/022* (2013.01); *G01N 29/036* (2013.01); *B81B 2201/0271* (2013.01); *B81B 2201/058* (2013.01); *G01N 2291/0427* (2013.01)

(58) Field of Classification Search
CPC .... G01N 15/06; G01N 29/022; G01N 29/036; G01N 2291/0427
See application file for complete search history.

(56) References Cited

U.S. PATENT DOCUMENTS 6,866,819 B1 * 3/2005 Chandra ................ G01N 27/12
422/50
6,925,392 B2 8/2005 McNeil, III et al.
(Continued)

FOREIGN PATENT DOCUMENTS

| CN | 110711613 | 1/2020 |
|---|---|---|
| KR | 10-2012-0085263 | 7/2012 |
| TW | 273222 | 2/2007 |

OTHER PUBLICATIONS

Lee, Jungchul; King, William P. Array of microcantilever heaters with integrated piezoresistors. Aug. 2007, International Conference on Nanotechnology (Year: 2007).*

(Continued)

*Primary Examiner* — Tarun Sinha
(74) *Attorney, Agent, or Firm* — Tenley Krueger; C. Tumey Law Group PLLC

(57) ABSTRACT

A method is disclosed comprising determining a concentration of one or more compounds of a fluid in an industrial water operation in real time. The determining of the concentration of the one or more components comprises contacting an array of sensors of a microelectromechanical system (MEMS) device with a sample of the fluid to provide a sample response indicative of the concentration of the one or more components. The method further provides adjusting or maintaining at least one operating parameter of the industrial water operation based on the concentration of the one or more components of the fluid.

20 Claims, 8 Drawing Sheets

(51) Int. Cl.
*G01N 29/02* (2006.01)
*G01N 29/036* (2006.01)

(56) References Cited

U.S. PATENT DOCUMENTS

| | | | |
|---|---|---|---|
| 7,068,027 B1 * | 6/2006 | Mastro | G01N 27/74 |
| | | | 324/204 |
| 7,392,697 B2 | 7/2008 | Chikenji et al. | |
| 7,493,799 B1 * | 2/2009 | Discenzo | F16C 19/52 |
| | | | 184/108 |
| 7,595,876 B2 | 9/2009 | DiFoggio | |
| 7,712,527 B2 | 5/2010 | Roddy | |
| 8,297,353 B2 | 10/2012 | Roddy et al. | |
| 8,302,686 B2 | 11/2012 | Roddy et al. | |
| 8,316,936 B2 | 11/2012 | Roddy et al. | |
| 9,709,429 B2 | 7/2017 | Chatterjee et al. | |
| 9,856,139 B2 | 1/2018 | Huang et al. | |
| 10,358,914 B2 | 7/2019 | Roberson et al. | |
| 11,060,400 B1 | 7/2021 | Jamison et al. | |
| 2003/0121799 A1 | 7/2003 | Stevens et al. | |
| 2006/0257286 A1 * | 11/2006 | Adams | G01N 29/4418 |
| | | | 422/82.01 |
| 2007/0202626 A1 * | 8/2007 | Liu | H01H 57/00 |
| | | | 438/48 |
| 2013/0233796 A1 | 9/2013 | Rao et al. | |
| 2016/0161459 A1 | 6/2016 | Rouse et al. | |

OTHER PUBLICATIONS

Samco, Treated vs. Untreated Cooling Tower Water Risks for your plant, Oct. 2016. Available at https://www.samcotech.com/treated-vs-untreated-cooling-tower-water-risks-problems/, Accessed May 1, 2021.

Powergen International, Four Boiler contaminants that jeopardize power plant operation and maintenance, Feb. 2014.

Halliburton, ICE core technology, SPE2013, Oct. 1, 2013. Available at https://www.offshore-mag.com/business-briefs/equipment-engineering/article/16772543/spe-2013-halliburton-rolls-out-ice-core-downhole-fluid-analysis-technology.

International Search Report and Written Opinion for Application No. PCT/US2021/043858, dated Apr. 12, 2022.

\* cited by examiner

METHODS AND SYSTEMS FOR CHARACTERIZING FLUID COMPOSITION AND PROCESS OPTIMIZATION IN INDUSTRIAL WATER OPERATIONS USING MEMS TECHNOLOGY

BACKGROUND

An industrial water operation may be any process or system that circulates water as its primary ingredient. Many industrial water operations, such as cooling towers, boilers, forming sections of a paper making process, and waste treatment systems use chemical treatment products for improved energy efficiency, waste reduction, asset protection, and improve product quality. Typical treatment products for industrial water systems control scaling, corrosion, fouling, foaming, odor formation, and microbiological growth.

To achieve optimum performance from the chemical treatment, products introduced into the industrial water operation may require a feed strategy. For example, a typical industrial water operation, as used in cooling towers, may employ a control system that may be set up to feed treatment product based on either a bleed/feed mechanism, wherein the action of blowdown triggers a chemical feed pump or valve that feeds treatment product; or, in the alternative, the control system may feed treatment product based on a certain amount of make-up water being pumped. Systems for blending and feeding liquid chemicals into industrial water operations may be based on one or more sensor technologies, such as load cell, level sensor, and volumetric measuring devices to measure the amount of chemical dispensed. In some cases, a characteristic measurement of the liquid may be used to determine the mixture concentration.

BRIEF DESCRIPTION OF THE DRAWINGS

These drawings illustrate certain aspects of some of the examples of the present disclosure and should not be used to limit or define the disclosure.

DETAILED DESCRIPTION

Figure 1:
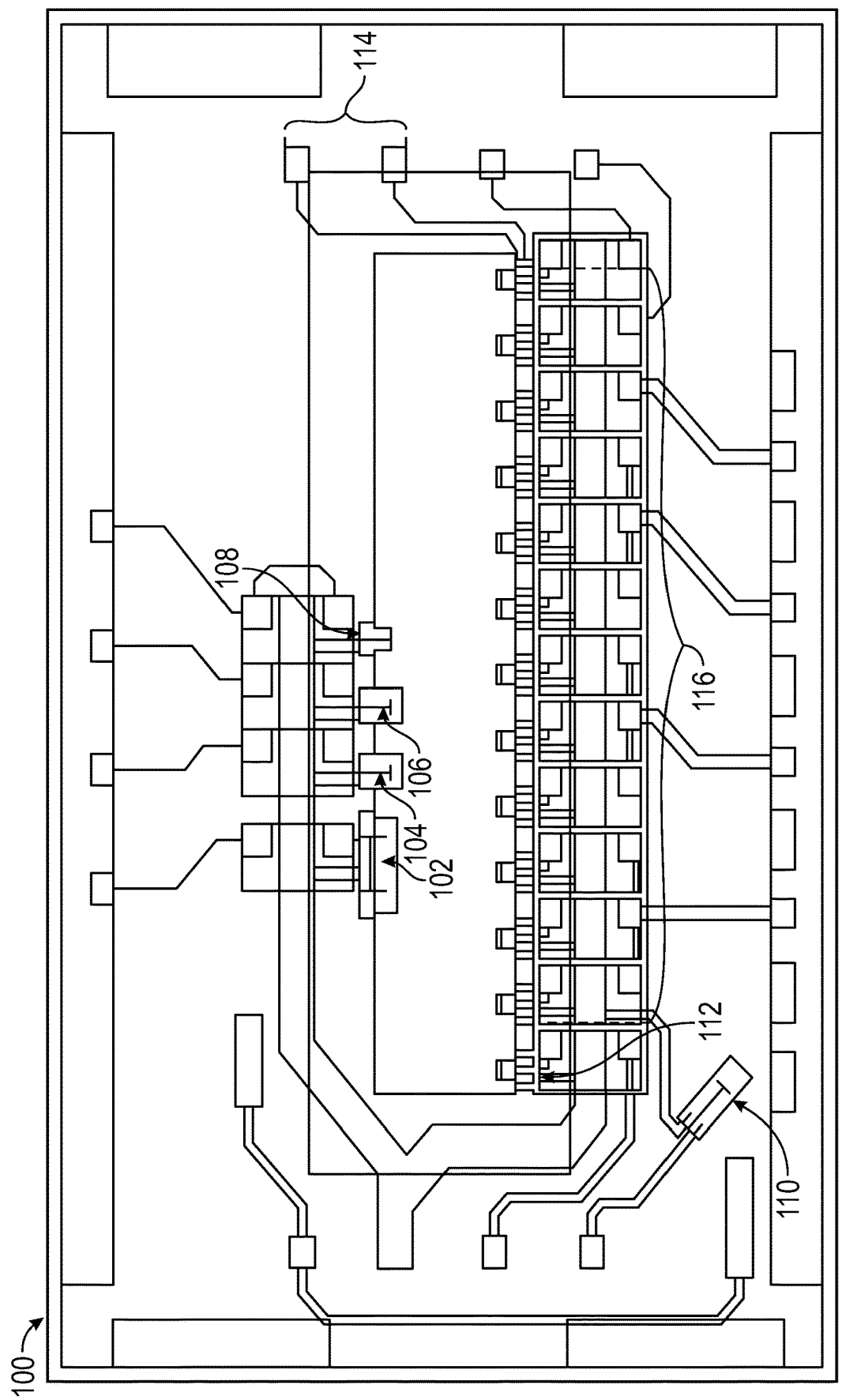
FIG. 1 is a schematic of a sensor or "molecular property spectrometer (MPS), according to the present disclosure.

The present disclosure provides methods and systems for analyzing, monitoring, and controlling chemical treatment concentrations in industrial water operations using micro-electro-mechanical systems (MEMS) in real time.

The ability to analyze and monitor specific variables in industrial water operations in real-time may reach across multiple industries where water may be utilized. Some examples of industrial water operations for methods and systems disclosed herein may include, but may not be limited to, cooling towers, boilers, wastewater treatment facilities, refinery process water, and ammonia plants. Industrial water operations may also include, but may not be limited to, hot water systems; mineral process waters comprising mineral washing, flotation, and benefaction; papermaking processes; black liquor evaporators; gas scrubbers; air washers; continuous casting processes; air conditioning systems; refrigeration systems; pasteurization processes; water reclamation systems; water purification systems; membrane filtration water systems; and food processing streams.

As disclosed herein, water may include pure water, tap water, fresh water, brine, steam, and/or any chemical, solution, or blend that may be circulated in an industrial water operation. Common contaminants in industrial water operations may include but may not be limited to calcium, magnesium, iron, copper, aluminum, silica, silt, oil, and combinations thereof. In other examples, as disclosed herein, such as power plant operation and maintenance, critical contaminants may include, but may not be limited to, dissolved oxygen, hydrazine, sodium, silica, and combinations thereof. Contaminants may also include, but may not be limited to, pollutants such as detergents, dyes, pharmaceuticals, petroleum products, oil, grease, heavy metals, biological and non-biological organic products, food and beverage wastes, and combinations thereof. The most common chemical treatments for contaminants in industrial water operations include, but are not limited to, orthophosphate, dispersant polymers, azole, phosphonobutanetricarboxylic acid ("PBTC") and salts thereof, and phosphinosuccinic oligomer ("PSO") chemistries.

For example, in power plant operation and maintenance, oxygen contamination of steam condensate may lead to inefficient or improper feedwater aeration; air leakage at pump seals, receivers, and flanges; leaking heat exchangers; and ingress into systems that may be under vacuum. It may also promote localized pitting corrosion, which may cause rapid failure of critical equipment in the steam system. One way to control dissolved oxygen levels may include dosing boiler feedwater with oxygen scavenging chemicals, such as hydrazine. When these chemicals are used, the efficiency of the dosing regimen may be assessed by measuring for dissolved oxygen at the economizer or boiler inlet. Any fluctuations may be addressed by increasing or reducing the dose quantities. Any dramatic variations in oxygen levels during the load cycle of a plant, combined with different levels required for different boiler chemistry regimes, may require an analyzer that may offer a fast response across both high and low dissolved oxygen concentrations.

In some examples, sodium may be the root cause of many different types of corrosion in boilers. It is one of the most important parameters to measure in power plant applications. Traditionally, conductivity measurement has been used to indicate the total dissolved solids. However, it lacks the sensitivity to measure sodium at low levels. One particular problem with sodium is the cycle it may undergo during hydrolysis. During this process sodium carbonate may be turned into sodium hydroxide, which then attacks iron in the boiler. As iron dissolves, it may form sodium ferrate, which under hydrolysis may regenerate into sodium hydroxide. Prolonged exposure to this cycle may put boiler components, such as bends and joints under constant attack, thereby causing them to become embrittled and increasing the risk of leaks and cracks. If carried over in the steam, sodium may also build up on critical components as the steam condenses, including the steam turbine, where it may attack the turbine blades. The importance of safeguarding against sodium means that sodium levels should be measured at key points in the steam generation and distribution loops. For example, sample points may include the water treatment plant, the condenser extractor pump, the polishing plant outlet, and the saturated and superheated steam distribution loops.

At the water treatment plant, monitoring for sodium may help to identify any breakthrough from the cation exchange and mixed bed outlets caused by exhaustion of the ion exchange beds. As sodium is a monovalent ion, it may be more likely to break through first, providing an early indicator of bed exhaustion. As such, monitoring for sodium may also act as a useful measure of bed efficiency as well as a precursor measurement for potential sodium contamination further down the line. Online measurement of sodium after the extraction pump may provide a useful indicator of condenser leaks. Operated under high vacuum, the condenser may be prone to leaks that cause cooling water to become mixed with the condensate. In high pressure boilers, any chemical contaminants present in the steam may quickly build up in the boiler drum and may be carried over in the steam to the turbine. Monitoring for sodium in the saturated and superheated steam distribution loops may help to protect against corrosion and the formation of sodium salts on the super heater or turbines caused by steam carryover. By measuring the purity of the steam and comparing it to the measurements taken from the saturated steam before the superheater and condensate stages, an assessment of whether quality may be affected by issues, such as deposition of sodium salts or condenser leaks may be completed. The same assessment or measurement may also be determined for once-through boilers.

In some examples, silica may cause build-up of hard and dense scale inside the boilers and turbines of power generation plants. Silica has a very low thermal conductivity and may form a dense, porcelain-like scaling that may not be removed even with acid. For example, even a 0.5 mm build-up of silica may reduce thermal transfer by 28 percent, reducing efficiency, leading to hot spots and eventual rupturing, ultimately resulting in plant failure. Silica buildup may be controlled through an effective monitoring regimen. Similar to sodium, silica may be measured at multiple points around the steam system, including the demineralization plant, boiler feedwater, boiler drums, superheater, and condenser outlets. Measuring silica in the steam from the boiler, either at the superheater or at the entrance to the turbine, may provide a good indicator of overall steam purity. Provided that the silica concentration may remain below 20 parts per billion, the level of scale deposit may be minimal. Unlike many other potential contaminants, dissolved silica may be only very weakly ionized, so it may not be detected using a simple conductivity measurement. It may require a dedicated monitor.

Some industrial water operations may require a cooling tower water treatment system. Common issues arising from improperly treated cooling tower feed water may include scaling, corrosion, fouling, and biological growth. When water is heated, certain compounds that may be soluble in low-temperature waters may become insoluble in high-temperature water and may scale on surfaces within the cooling tower if left untreated, plugging up and subsequently damaging pipes and internal surfaces and equipment. Some common compounds that scale cooling towers may include, but may not be limited to, calcium carbonate, calcium phosphate, magnesium silicate, and silica. In addition to temperature, alkalinity (pH) may also play a role on scaling within a cooling tower. As pH increases, many scale-forming compounds may decrease in solubility, thereby precipitating out in higher rates when the water is heated.

In some examples, corrosion may occur in cooling towers when certain contaminants in the water, mainly gasses, such as oxygen and carbon dioxide, may cause the metal to degrade and return to its oxide state by means of an electrical or electrochemical reaction. This may thin areas in the metal that may increase chances of rupture. Different types of corrosion commonly seen in cooling towers include, but may not be limited to pitting, general corrosion, and galvanic corrosion. Pitting may be extremely destructive because it may be concentrated on small areas; may be difficult to detect; and may perforate metal in a short timeframe. General corrosion may occur evenly across the surface of the metal and may contribute to fouling, thereby reducing system efficiency. Galvanic corrosion may occur when two different metals come into contact long enough to conduct electricity. The electrical differences may attack more active metal, thereby corroding it rapidly. In addition to dissolved gasses, some other factors that may lead to corrosion in a cooling tower include, but may not be limited to, bacterial contaminants; variations in temperature, alkalinity (pH), dissolved and/or suspended solids.

In some examples, fouling may occur in cooling tower water similar to scaling. For example, fouling may accumulate deposits, but these deposits may not be as hard as scale. Some contaminants that may cause fouling may include, but may not be limited to, colloidal and suspended solids, biological contaminants, silt, sand, and combinations thereof. Further, the growth of microbiological contaminants in cooling tower water, such as bacteria, algae, and fungi, may also cause all of the aforementioned issues: corrosion and fouling of cooling tower equipment. Biological growth may occur in any kind of cooling tower system, but may happen most in open-loop systems, whereby the cooling tower water may be more readily exposed to the elements and favorable environments for biological growth.

In the refining of crude oil (refineries), water may be utilized in several different processes to aid in the removal of solids and other constituents. During transportation of the crude oil to the refinery, water may be used as ballast material in ships and water may be entrained within the crude oil with salts and solids. The ability to accurately measure and quantify the presence of the water in the crude oil may be critical in determining crude oil quality and potential discounts (pricing) due to the presences and volume of the water. The higher the volume of water present the higher the discount. Additionally, the higher the volume of water the increased potential of other contaminants, such as, but not limited to, salts, solids and unstable asphaltenes. The ability to identify the presence and measure the volume of these contaminants may aid in the processing of crude oil in the refinery processes. Additional parameters which may be determined by the MEMs Technology of the crude oil are paraffins, isoparaffins, olefins, naphthenes, aromatics, saturates, resins and asphaltenes (PIONA/SARA) components. The ability to determine some or all of these components may aid in the management of equipment fouling, microbiological growth, corrosion, emulsion resolution and refinery product yield.

In some examples, water may be utilized in the crude oil refinery process to remove contaminants from crude oil in the desalter process. Before and at the crude oil desalter, water may be injected into the crude oil. The water may contact the water, solids, salts, and other contaminants contained in the crude oil. These contaminants and other water-soluble constituents may be "washed" from the crude oil phase into the water phase. The "wash water" may be injected upstream of the desalter vessels and, prior to entering the desalter, the water/oil may pass through a "mix valve" that may shear the water molecules into a fine emulsion, which may aid in the water molecules contacting contaminants. Chemical emulsion breakers and reverse breakers may be added to this process to separate the fine emulsions. The desalter vessels may utilize three mechanisms to separate the water/oil emulsion, residence time, electricity, and chemicals. The residence time may be in the form of reduced flow of the fluids as they enter the desalter, allowing for the oil to separate from the water with the heavier fluid to drop, and the lighter fluid to rise. Next, electrical grids may provide an electrical field forcing water molecules to polarize, lining up positive and negative fields within the water molecules to coalesce and bond together, thereby forming larger water drops. Lastly, chemical emulsion breakers and/or reverse breakers may remove interstitial films on water/oil molecules, thereby allowing/improving the coalescing process. During this process, the volume of contaminants removed may be measured by analyzing the water entering and exiting the desalter vessel. The amount of contaminants removed directly impacts downstream refining processes. The more contaminants removed, the more efficient the refining process (reduced fouling and corrosion).

In some examples, in various processes in multiple types of units, water may be utilized as wash water to aid in diluting acids, removing solids, preventing solids from forming and removing salts. The most common and more critical of these examples may be the refinery atmospheric tower overhead system. This system processes the lighter end hydrocarbon (light gases and naphtha). During this process, any salt contaminants and water from steam injections enter the top of the atmospheric tower, flow overhead, and may be cooled by heat exchangers from gases to liquids. During this cooling process, amine and ammonia combine with chloride salts to form deposits. As these deposits cool, they may become water-wet with condensate (from steam injected into the tower to aid in the distillation process). Once water-wet, severe/aggressive acids form which may lead to catastrophic failures of the crude atmospheric tower overhead system. These failures may result in leaks, fires, reduced refinery throughput, and refinery shutdowns. Monitoring the chloride, ammonia, pH, iron, and other constituents of this water may be critical to maintaining the system's reliability. Other examples of water utilized as wash water in similar processes include, but are not limited to, coker unit combination tower overheads, light end fractionator overheads, stripper tower overheads, vacuum unit overheads, hydrotreater unit overheads, and hydrocracker unit overheads.

Utilizing MEMS technology in the methods and systems disclosed herein may improve chemical treatments in industrial water operations by analyzing treatment chemical concentration, as well as their efficacy, substantially in real-time. The MEMS disclosed herein may comprise multiple, complementary chemical sensors on a single silicon chip, often referred to as the Molecular Property Spectrometer™ (MPS™). MPS™ sensors may work together to measure a variety of thermodynamic and electrostatic molecular properties of sampled vapors, liquids, and particles. As disclosed herein, the terms "MPS chip", MEMS chip"," MPS", "MEMS", or simply "chip" may be used interchangeably. The chemical sensing elements of the MEMS sensors disclosed herein may detect corrosion by-products and levels substantially in real-time, thereby resulting in better process monitoring and control, improved operation efficiency, and reduced maintenance and downtime.

Generally, MEMS devices may include mechanical and electrical features formed by one or more semiconductor manufacturing processes. For example, MEMS devices may include micro-sensors that may convert electrical signals into mechanical signals. In some applications, MEMS devices may be electrically connected to application-specific integrated circuits (ASICs), and to external circuitry, to form complete MEMS systems.

The MPS™ chip may create a large dataset of chemical information. More specifically, the number of cantilever devices contained in a chip may be the number of data points in a dataset. For example, 10 cantilevers may yield 10 responses in the dataset. the process may use multiple chips, wherein each chip may have a set of cantilevers. Hence, the size of one timed dataset may be determined by the configuration of the chip as well as the number of chips. Some examples may require a predetermined test temperature for sampling, whereby the elapsed time between datasets may be expanded to allow for heating or cooling of the sample. In other examples, testing may be on a scheduled basis. For example, samples may be tested 2 times per day, 4 times per day, 6 times per day, 8 times per day, etc. Thus, the testing schedule may impact the amount of data.

In some examples the MPS™ chip may create a large dataset of chemical information may be created in less than 120 seconds, less than 90 seconds, less than 60 seconds, less than 30 seconds, less than 10 seconds, or less than 1 second. In essence, the MPS™ chip disclosed herein is an example of a MEMS with the inherent advantages of low power consumption, minute size, light weight, and robustness. In other examples, the MEMS may heat to hundreds of degrees Celsius within a span of milliseconds. The MEMS may produce a plurality of high-precision measurements or high-precision thermal measurements, then cool back to room temperature. Specific measurements may include, but may not be limited to, parts per million of a selected group of analytes, wherein the analytes may comprise anti-corrosion chemicals, anti-scaling chemicals, algaecides, friction reducers, and combinations thereof. Typically, friction reducers may inhibit the onset of turbulent flow. For example, the friction reducer may change the transition from laminar to turbulent flow from a 2000 Reynolds number to a 4000 Reynolds number. Further, the MEMS may detect picogram-scale masses and measure temperature with at least a 0.01-degree resolution or greater. Moreover, the MEMS may operate in temperatures from about −40° C. to about 70° C., and all non-condensing humidity levels. Alternatively, the MEMS may operate in temperatures from about −40° C. to about 70° C., about −30° C. to about 60° C., about −20° C. to about 50° C., about −10° C. to about 40° C., about 0° C. to about 30° C., or about 10° C. to about 20° C., and all non-condensing humidity levels.

As disclosed herein, the MEMS comprising the MPS chip or sensor may comprise a plurality of cantilever elements having unique characteristic resonance which may depend on the various configurations. The exterior of the cantilever elements may comprise polymeric, analyte specific coatings. Thus, selected polymer coatings may have unique chemical and surface interactions with a test sample that may be manifested in a resonance frequency of each cantilever element in the MEMS chip. By utilizing a plurality of coatings, the resonance frequency response of each cantilever element may provide a unique signature for the chemical properties of the sample. Any coating that may interact with an analyte to change the resonance frequency may be used. For example, the cantilever element may comprise a polymer coating, a metal/piezoelectric sandwich, and a silicon coating with piezoresistive heater. The polymer coating may be used for analyte absorption, whereas the silicon coating with piezoresistive heater may be used for temperature control and heat pulses. The metal/piezoelectric sandwich may be used for drive/sense for frequency detection, as an impedance sensor, and as a temperature sensor. The integrated piezoelectric sensing elements that may provide electrical actuation and sensing of resonance frequency. Monitoring resonance may be a highly sensitive method of measuring very small masses of adsorbed analyte, wherein the adsorbed analyte may be less than 30 milligrams, less than 20 milligrams, less than 15 milligrams, less than 10 milligrams, or less than 5 milligrams. The piezoelectric configuration of the MEMS may allow an array of sensors to be electrically monitored rather than using an optical readout. The polymeric coating on the MEMS may be specific to the chemical being detected. In essence, the methods and systems of the industrial water operations incorporate analyte specific MEMS, wherein the methods and systems are essentially free of measurements that require tagging.

Typically, sampling occurs in a temperature-controlled environment to ensure the accuracy of measurements. However, responses may be modeled over a selected temperature range with a correction factor or model for the adsorption rate of specific analytes, as well as the base fluid density. Pressure may also be monitored if the MEMs device is exposed to pressures that may change the density of the particular fluid. Generally, as disclosed herein, pressures may be less than 300 psi, less than 250 psi, less than 200 psi, or less than 150 psi.

The methods and systems disclosed herein may present surprising results as sensor technology currently used in industrial water operations are generally limited to reading specially formulated chemical treatment chemicals to read traced and/or tagged chemistry. More specifically, current methods utilize sensor technology that may rely on inert tracer additives and luminescence of specific polymer molecules. There may be a plurality of inherent errors with the currently used process, in part due to the required special chemical formulations and the increased cost of chemical analysis. The methods disclosed herein for analyzing and monitoring industrial water operations comprise MEMS that may be configured to provide analytical quality data for chemical content that may be used to automate treatments in real time.

The methods disclosed herein further comprise water contacting an array of MEMS sensors, wherein the sensors measure contaminants present and the corresponding treatments for the specific contaminants. More specifically, the present disclosure may provide methods and systems for analyzing and measuring industrial water operations comprising measuring a sample response; treating the sample with a chemical additive that may selectively change a MEMS response to a specific analyte (wherein the chemical additive may be an acid, base, enzyme, or oxidizer); and measuring the treated sample; comparing the change in MEMS response to a calibrated curve; determining the analyte concentration of the sample.

The present disclosure may provide a method comprising determining a concentration of one or more components of industrial water or fluid; adjusting or maintaining at least one operating parameter of an industrial water servicing operation based on the determining of the concentration of the one or more components, wherein the industrial water or fluid comprises a fluid obtained from an industrial water operation during the industrial water servicing operation, wherein the determining of the concentration of the one or more components comprises contacting an array of MEMS sensors with at least a sample of the industrial water or fluid to provide a sample response indicative of the concentration of the one or more components.

More specifically, after contacting the array of MEMS sensors with the sample to provide the sample response, the determining of the concentration of the one or more components of the industrial water or fluid may further comprise: providing a treated sample by treating the sample to selectively alter a response of the MEMS device; contacting the array of MEMS sensors with the treated sample to provide a treated sample response; and utilizing a difference between the treated sample response and the sample response with calibration to curves to determine the concentration of the one or more components of the industrial water or fluid. In some examples disclosed herein, treating the sample may further comprise treating the sample with a chemical additive that may selectively alter the response of the MEMS device, wherein treating the sample may further comprise treating the sample with a chemical additive that may selectively alter the response of the MEMS device. In some examples disclosed herein, the chemical additive may include, but may not be limited to, an acid, a base, an enzyme, an oxidizer, a reducer, an antioxidant, an oxygen scavenger, a free radical source, a free radical trap, or a chemical reactant. In some examples disclosed herein, the sample response may be provided via resonance frequency, temperature, impedance, or combinations thereof within the MEMS device.

In some examples disclosed herein, a method may comprise: determining a concentration of one or more components of industrial water or fluid in one or more samples of industrial water or fluid; adjusting or maintaining one or more operating parameters of the industrial water operation based on the determining of the concentration of the one or more components in the one or more samples of the industrial water or fluid, wherein the determining of the concentration of the one or more components may comprise, for each of the one or more samples, contacting an array of MEMS sensors with the sample of the industrial water or fluid to provide a sample response indicative of the concentration of the one or more components. The adjusting or maintaining the one or more operating parameters based on the determining of the concentration of the one or more components may be at least partially automated. Moreover, the determining the concentration of one or more components of the industrial water or fluid in the one or more samples of the industrial water or fluid may be performed substantially in real-time. The method may further comprise monitoring a trend in the determined concentration of one or more components of the industrial water or fluid in the one or more samples of the industrial water or fluid and utilizing the monitoring of the trend in the adjusting or maintaining of the one or more operating parameters. As disclosed herein, parameters may include, but may not be limited to, a corrosion rate; a scaling rate; a deposition rate; a heat transfer rate; a cooling tower efficiency; a chemical concentration; a cycle of concentration; a suspended solids measurement; a dissolved solids measurement; a microbiological activity rate; a chemical activity rate; a process performance parameter; a product performance parameter; multiples thereof; combinations thereof; and multiples and combinations thereof.

As disclosed herein, a system for servicing an industrial water operation may comprise: at least one MEMS device operable for determining a concentration of one or more components of an industrial water or fluid via a sample response indicative of the concentration of the one or more components, wherein the sample response may be obtained by contacting an array of MEMS sensors with a sample of water or fluid, wherein the MEMS may comprise an array of cantilever elements, wherein the cantilever elements may comprise integrated piezoelectric sensing elements, wherein the cantilever elements may comprise a polymer coating, a metal/piezoelectric sandwich, and silicon with a piezoresistive heater; and a feedback system operable to adjust or maintain one or more operating parameters of the servicing of the wellbore based on the determined concentration of the one or more components; wherein the system may provide substantially real-time determining of the concentration of the one or more components of the industrial water or fluid, and wherein the system may be at least partially automated. The array of microcantilevers may comprise, for each of the one or more components, one or more microcantilevers comprising a coating sensitive to an analyte specific to each of the one or more components.

In some methods disclosed herein, a focused sampling system may be utilized. More specifically, one or more samples of water or fluid may be obtained from process equipment, such that one or more samples may have a desired purity (e.g., a contamination level below a maximum contamination level). The maximum contamination (or "threshold") level may include a total amount of about 1 to about 15 weight percent of one or more contaminants. Alternatively, the threshold contamination level may include a total amount of about 1 to about 15, about 2 to about 14, about 3 to about 13, about 4 to about 12, about 5 to about 10, or about 6 to about 9 weight percent of one or more contaminants. The one or more contaminants may include components of water or fluid that may not be present in the make-up water or fluid and/or present in the make-up water or fluid at a level greater than a level thereof in the process water.

The focused sampling system may include a sample line having a sample line inlet and a sample line outlet; a guard line having a guard line inlet and a guard line outlet; a common line having a common line inlet and a common line outlet, wherein the common inlet is fluidly connected with the sample line outlet and the guard line outlet, and wherein the common line outlet may be fluidly connected with a pump suction side inlet; the pump, wherein a discharge side outlet of the pump is fluidly connected with a discard line and a sample line, wherein the sample line is fluidly connected with one or more sample chambers; one or more MEMS positioned on the guard line, the sample line, the common line, or a combination thereof; and a flow restrictor operable to prevent flow of fluid from the guard line to the common line.

The focused sampling system may be partially automated, while also providing an option for manual sampling. Hence, according to one or more aspects of the present disclosure, an information handling system or computer equipment may be employed. For purposes of this disclosure, an information handling system may include any instrumentality or aggregate of instrumentalities operable to compute, classify, process, transmit, receive retrieve, originate, switch, store, display, manifest, detect, record, reproduce, handle, or utilize any form of information, intelligence, or data for business, scientific, control, or other purposes. For example, an information handling system may be a personal computer, a network storage device, or any other suitable device and may vary in size, shape, performance, functionality, and price. The information handling system may include random access memory (RAM), one or more processing resources, such as a central processing unit (CPU) or hardware or software control logic, ROM, and/or other types of nonvolatile memory. Additional components of the information handling system may include one or more disk drives, one or more network ports for communication with external devices, as well as various input and output (I/O) devices, such as a keyboard, a mouse, and a video display. The information handling system may also include one or more buses operable to transmit communications between the various hardware components. The information handling system may also include cloud storage and retrieval.

Figure 2:
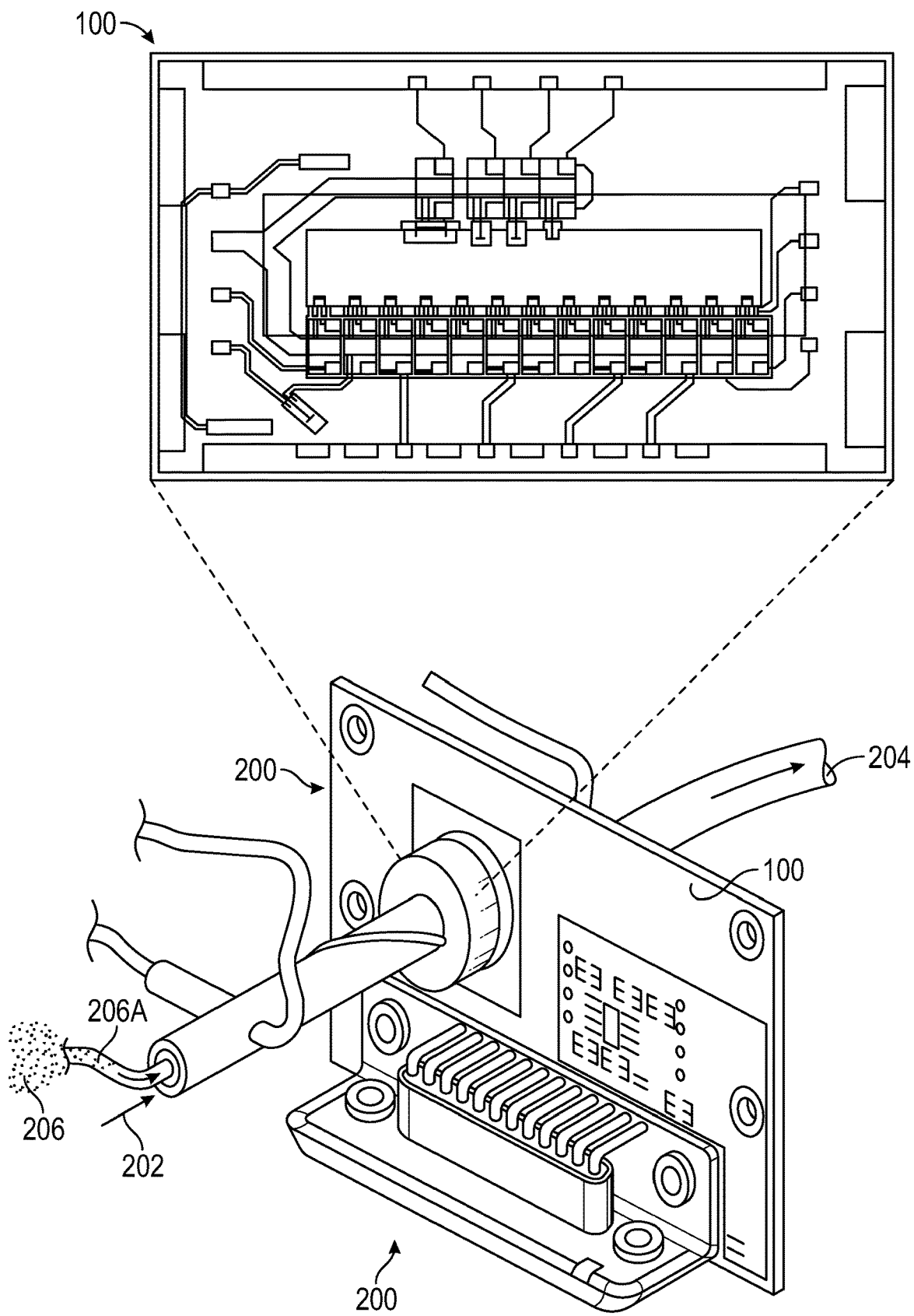
FIG. 2 is a schematic of a MEMS device including a chip of FIG. 1, according to the present disclosure.

Referring now to FIG. 1, wherein FIG. 1 is a schematic of an MPS chip or sensor 100, as disclosed herein. MPS chip 100 comprises a surface stress sensor 102, a calorimeter 104 (e.g., a polymer coated calorimeter 104), a thermometer calorimeter 106, an anemometer 108, a thermistor 110, a thermobalance 112, an impedance sensor 114, and polymer coated thermobalances 116. One or a plurality of MPS chips 100 may be incorporated into a MEMS device 200, as depicted in FIG. 2. FIG. 2 is a schematic of a MEMS device 200 comprising an MPS chip 100, a sample intake line 202 may be utilized to introduce a sample 206A of water or fluid 206 to MEMS device 200, whereby the sample 206A of water or fluid 206 may contact MPS chip 100. A sample outlet line 204 may be utilized to remove sample 206A of the water or fluid 206 from the MEMS device 200.

Continuing with FIG. 2, the MEMS device 200 may include a plurality of MPS chips or sensors 100 within a housing (not shown). In some aspects of the present disclosure, the housing (not shown) may include a housing of a sampling device 516 (see FIG. 5) including the MEMS device 200. For example, the MEMS device 200 may be within a sampling device 516 configured to obtain a clean water or fluid sample, in which case, the housing of the sampling device 516 may also provide the housing for the MEMS device 200. In alternative embodiments, for example, when MEMS device 200 is outside (e.g., proximate) of sampling device 516, MEMS device 200 may have its own housing (not shown).

A plurality of MPS chips 100 may be utilized to provide redundancy and/or enable a desired frequency of measurement of the concentration of one or more components of water or fluid 206. Utilizing a redundancy of MPS chips 100 may allow for one or more MPS chips 100 being cleaned or purged, while another one or more MPS chips 100 may be online. Cleaning/purging of the MPS chips 100 may depend on the nature of the interaction of one or more components (e.g., the analyte) with the MPS chip 100 (e.g., with fresh water or fluid 206, heating (e.g., via piezoresistive heater(s) 306 described hereinbelow with reference to FIG. 3) to flash the analyte off the MPS chip 100, or the like may be utilized to clean spent MPS chips 100 prior to reuse.

Figure 3:
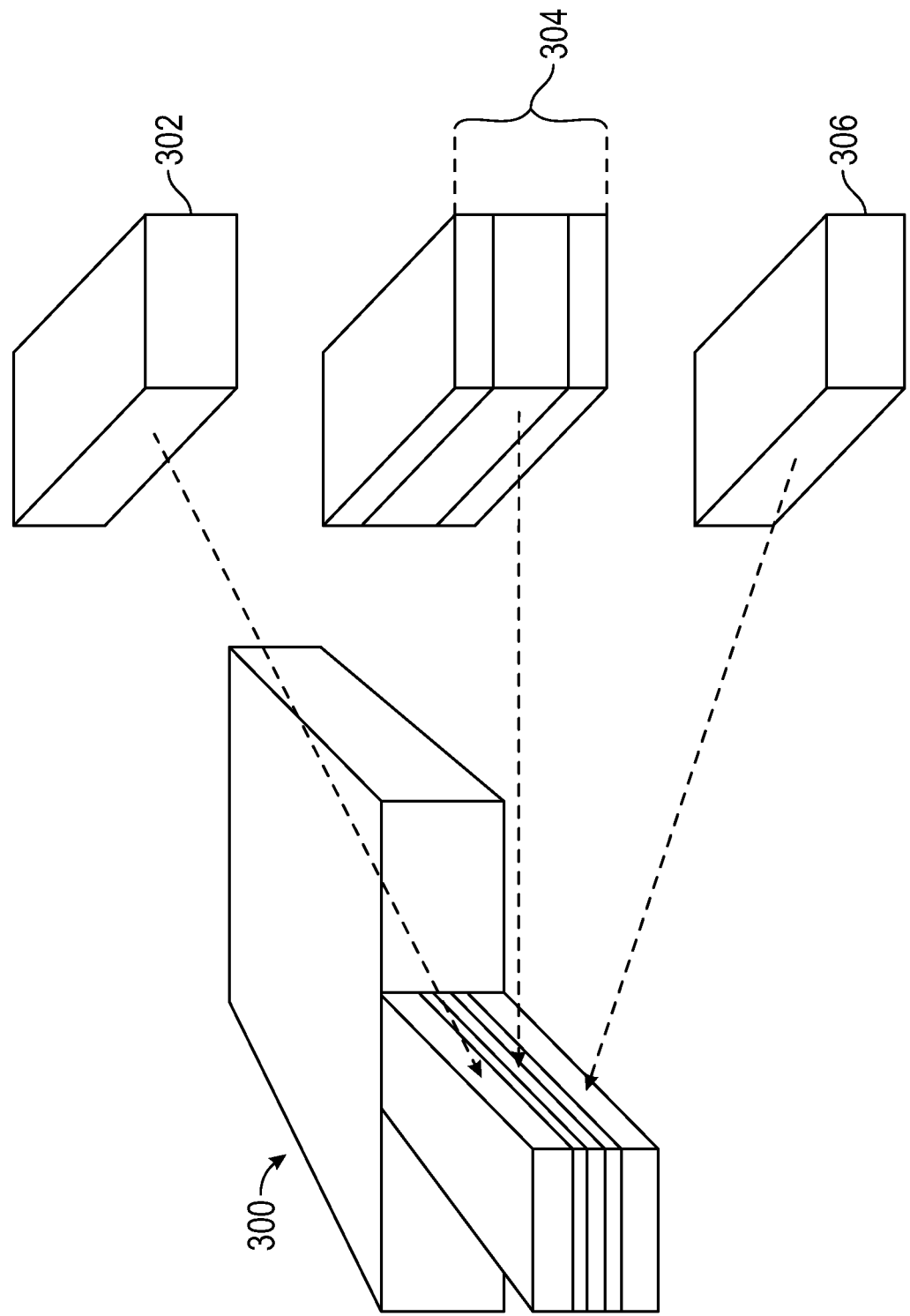
FIG. 3 is a is a schematic of a cantilever element of a chip of FIG. 1.

Referring now to FIG. 3, wherein FIG. 3 is a schematic of a cantilever element 300, MEMS device 200 may include an array of cantilever elements (e.g., microcantilevers) 300 with integrated piezoelectric sensing elements that may provide electrical actuation and sensing of resonance frequency. Cantilever element 300 may include coating 302, metal/piezoelectric sandwich 304, and silicon with piezoresistive heater 306. Coating 302 (e.g., polymer coating 306) may be operable for analyte absorption. Metal/piezoelectric sandwich 304 may provide drive/sense for frequency detection, impedance sensor, and temperature sensor. Piezoresistive heater 306 may provide for heat control (e.g., heat pulses). Resonance frequency, heat, and/or impedance may be utilized to determine the concentration of one or more components of the water or fluid 206. The resonances may be utilized to distinguish one or more components of the water or fluid 206.

Still referring to FIG. 3, an array of microcantilevers 300 may include, for each of the one or more components, one or more microcantilevers 300 including a coating 302 sensitive to an analyte specific to each of the one or more components (e.g., specific to the component itself or otherwise indicative of the component). As depicted in FIG. 3, the coating 302 of at least a portion of the array of microcantilevers 300 may include a polymer. MEMS device 200 may include a plurality of complementary chemical cantilevers 300 on each of the one or the plurality of MPS chips or sensors 100. The MPS chip or sensor 100 may, in certain aspects, rapidly (e.g., within a second) create a large, rich dataset of chemical information. Software may be utilized to identify the types of molecules (e.g., one or more components) present in the sample 206A of the water or fluid 206.

MPS chip or sensor 100 may incorporate an array of microcantilevers 300 with integrated piezoelectric sensing elements 304 that may provide electrical actuation and sensing of resonance frequency. Monitoring resonance may be a highly sensitive method of measuring very small masses of adsorbed analyte. An array of microcantilevers or sensors 300 may be electrically monitored via the MPS chip or sensor 100 due to the piezoelectric configuration provided by the MPS chip or sensor 100.

One or more of the microcantilevers 300 may include a built-in resistive heater 306 whereby an assortment of thermal analyses (e.g., Differential Scanning calorimetry or DSC) may be conducted. The resistive heater(s) 306 may allow for cleaning of each microcantilever 300/MPS chip or sensor 100 after processing a sample 206A of the fluid 206 to be analyzed. The resistors 306 may also enable temperature and flow compensation in order to minimize noise and drift of the piezoelectric sensors 304 and further enhance sensitivity.

The selected polymer coatings 302 may have unique chemical and surface interactions with the test sample 206A of the fluid 206. These unique chemical and surface interactions may be manifested in the resonant frequency of each cantilever element 300 in the MPS chip or sensor 100. By using many different coatings 302, the resonance frequency response of each cantilever element 302 may be designed to provide a unique signature for the chemical properties of sample 206A. Any suitable coating 302 that may interact with an analyte (e.g., each of the one or more components of the fluid 206) to change the resonance frequency may be utilized. The type of interactions may include sorption (e.g., the analyte (e.g., the component of the fluid 206) adsorbs or absorbs on the coating 302), dissolution/solvation (the analyte dissolves or solvated the coating 302), precipitation (the analyte precipitates on the coating 302) and/or other interactions. The chemistry and concentration of the sample 206A of the fluid 206 may be determined using this technology. Additionally, the MEMS device 200 may provide a heat source (e.g., piezoelectric heater 306) that may allow the signature to be thermally responsive. In some cases, impedance may be included (e.g., via metal/piezoelectric sandwich 304) in the MEMS device 200 to better differentiate chemical species and concentration.

Figure 4A:
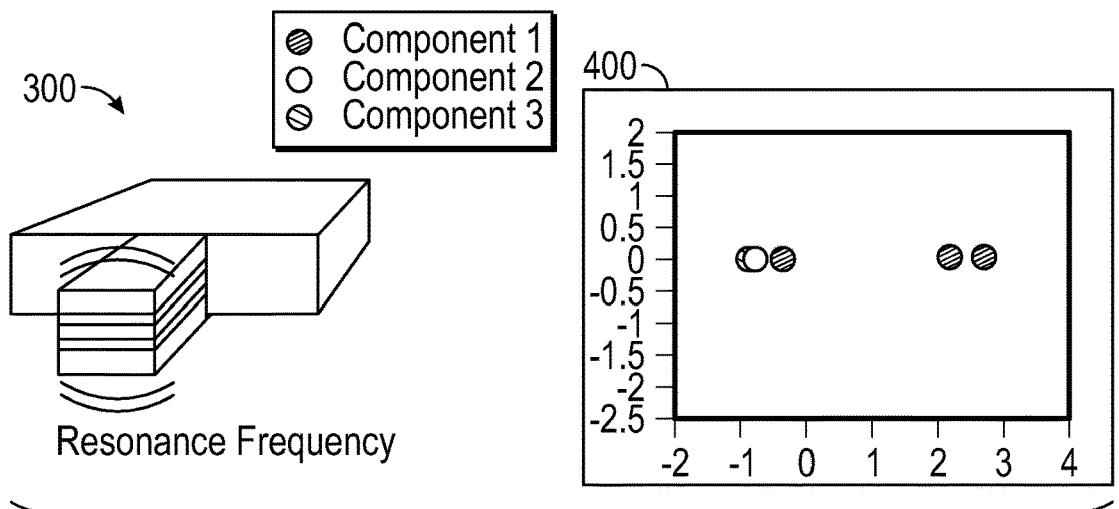
FIGS. 4A-4C are pictorial representations depicting how resonance frequency (FIG. 4A), resonance frequency and temperature (FIG. 4B), and resonance frequency, temperature, and impedance (FIG. 4C) may be utilized to distinguish one or more components of an industrial water operation.
Figure 4B:
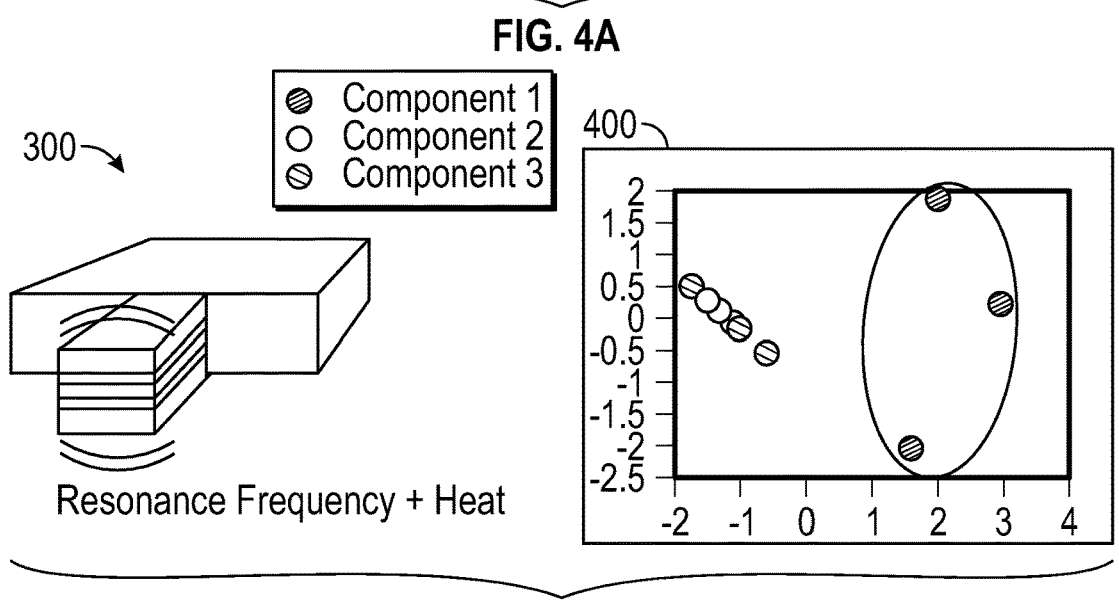
Figure 4C:
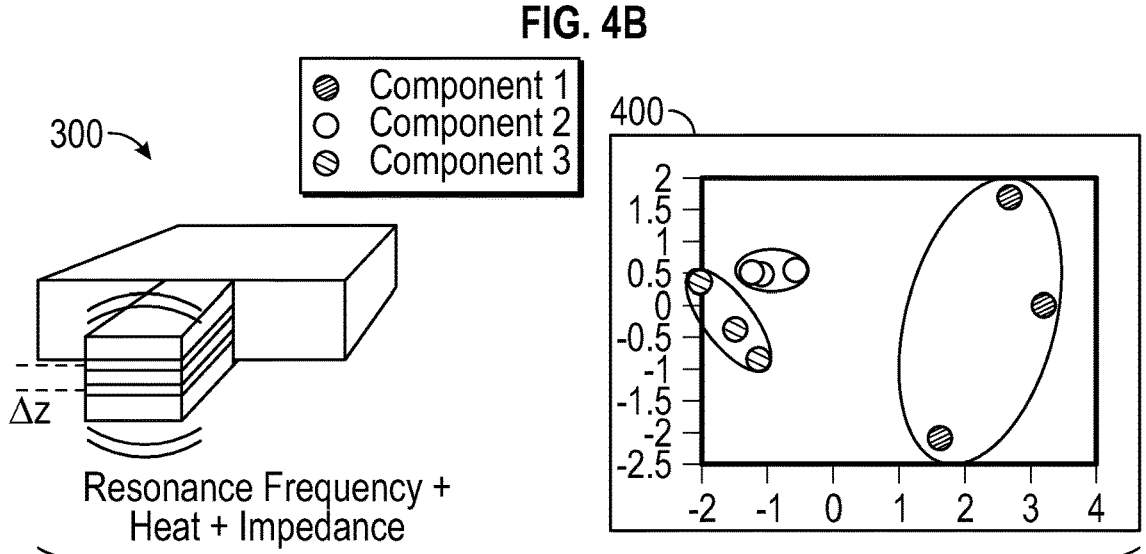

FIGS. 4A-4C are pictorial representations depicting how resonance frequency (FIG. 4A), resonance frequency and temperature (FIG. 4B), and resonance frequency, temperature, and impedance (FIG. 4C) may be utilized to distinguish one or more components of water or fluids in an industrial water operation (e.g., Component 1, Component 2, Component 3 depicted in FIGS. 4A-4C) of the water or fluid 206. Microcantilever 300 may be designed to determine resonance frequency, temperature, or impedance, and any combination thereof. The array of microcantilevers 300 may include, for each of the one or more components, one or more microcantilevers 300 including a coating 302 sensitive to an analyte specific to the each of the one or more components (e.g., specific to the component itself or otherwise indicative of the component). As depicted in FIG. 3, the coating 302 of at least a portion of the array of microcantilevers 300 may include a polymer. MEMS 200 may include a plurality of complementary chemical microcantilevers 300 on each of the one or the plurality of MPS chips or sensors 100. As depicted in FIGS. 4A-4C, the determined values of resonance frequency, temperature, and/or impedance may be transferred to an information handling system 400.

Figure 5:
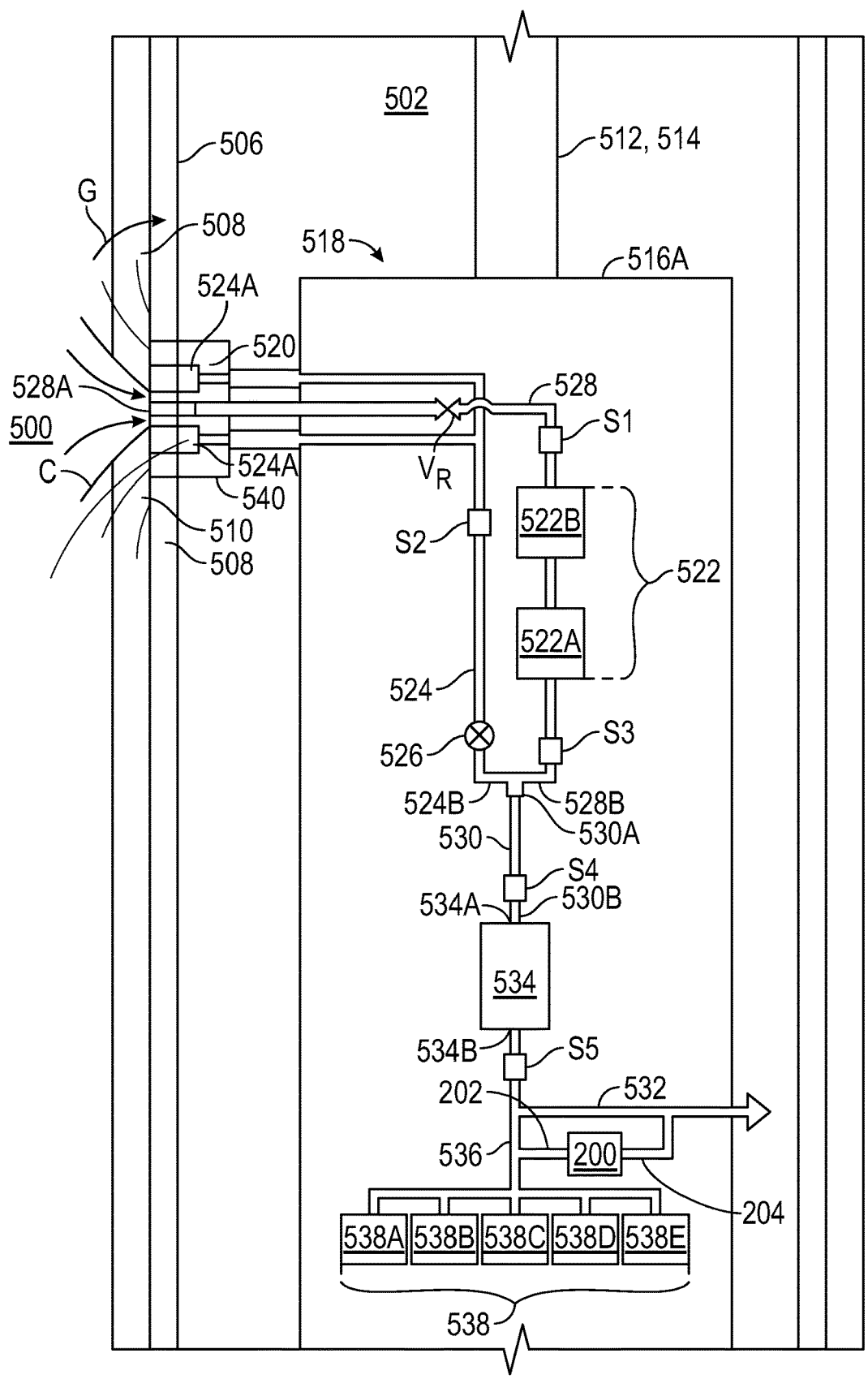
FIG. 5 is a schematic illustration of a focused sampling system of a general industrial water operation using MEMS, as disclosed herein.

Referring now to FIG. 5, which is a schematic of a focused sampling system 518 of a general industrial water or fluid operation using MEMS 200, as disclosed herein. Focused sampling system 518 includes sample line 528; guard line 524; common line 530; pump 534; discard line 532; sample line 536, one or more sample chambers 538 (with five, including first sample chamber 538A, second sample chamber 538B, third sample chamber 538C, fourth sample chamber 538D, and fifth sample chamber 538E depicted in the embodiment of FIG. 5; one or more fluid ID sensors S positioned on guard line 524, sample line 528, common line 530, or a combination thereof (with first fluid ID sensor S1 and third fluid ID sensor S3 depicted on sample line 528, second fluid ID sensor S2 depicted on guard line 524, fourth fluid ID sensor S4 depicted on common line 530, and fifth fluid ID sensor S5 depicted on pump outlet line 534B); and flow restrictor 526.

Sample line 528 may have a sample line inlet 528A and a sample line outlet 528B. Guard line 524 may have a guard line inlet 524A and a guard line outlet 524B. The focused sampling system 518 may include one or a plurality of lines that may extend from guard line inlets 524A thereof and merge to form a single guard line 524 toward guard line outlet 524B. This configuration of guard line 524 is intended to be included in the term "guard line(s) 524. In some examples disclosed herein, the guard line(s) 524 may be configured for a higher fluid flow rate QG than a fluid flow rate Qs of the sample line 528. Common line 530 may have a common line inlet 530A and a common line outlet 530B and may be fluidly connected with the sample line outlet 528B and the guard line outlet 524B, for example at a tee or Y junction. Pump 534 may have a suction side inlet 534A and a discharge side outlet 534B. Suction side inlet 534A of pump 534 may be fluidly connected with common line outlet 530B and discharge side outlet 534B of pump 534 may be fluidly connected with discharge line 532 and sample line 536, for example via a tee or Y junction. Sample line 536 may be fluidly connected with the one or more sample chambers 538.

Flow restrictor 526 may be operable to prevent flow of fluid from guard line 524 to common line 530 in a first (e.g., closed) configuration. In some examples disclosed herein, flow restrictor 526 may be a shutoff valve. In some embodiments disclosed herein, guard line(s) 524 may have a flow restrictor thereupon, such as a restrictor valve VR, that may be operable as a shutoff valve that may be actuated to prevent fluid flow through guard line 524. In some embodiments, a separate restrictor 526 may not be present. Flow restrictor 526 may be a check valve. Restrictor 526 may be positioned on guard line 524 upstream of guard line outlet 528B. Sample line 528 may include a check valve upstream of sample line outlet 528B in some examples disclosed herein.

The focused sampling system 518 may further include a probe defining a sample zone fluidly connected with the sample inlet line of the sample line, a guard zone fluidly connected with the guard line inlet of the guard line, or both a sample zone fluidly connected with the sample line inlet of the sample line and a guard zone fluidly connected with the guard line inlet of the guard line. For example, the focused system 518 may further include probe 520 defining sample zone 606 (see FIGS. 6A-6B) fluidly connected with the sample line inlet 528A of the sample line 528, and guard zone 604 (see FIGS. 6A-6B) fluidly connected with the guard line inlets 524A of the guard line 524.

The comparative flow rate QG in the guard line(s) 524 from guard zone(s) 604 (see FIGS. 6A-6B) and flow rate Qs in the sample line 528 from sample zone 606 (see FIGS. 6A-6B) may be represented by a ratio of flow rates QG/Qs. The flow rate into the sample line 528 from the sample zone may be represented by Qs and may also be referred to herein as the flow rate in the sample zone 606 (see FIGS. 6A-6B), and the flow rate into the guard line(s) 524 from the guard zone(s) 604 (see FIGS. 6A-6B) is represented by QG, and is also referred to herein as the flow rate in the guard zone(s) 604 (see FIGS. 6A-6B). The flow rate Qs in the sample line 528 from sample zone 606 (see FIGS. 6A-6B) may be selectively increased and/or the flow rate QG in the guard line(s) 524 from guard zone(s) 604 (see FIGS. 6A-6B) may be decreased to allow more fluid to be drawn into the sample zone 606 (see FIGS. 6A-6B). Alternatively, the flow rate Qs in the sample line 528 from sample zone 606 (see FIGS. 6A-6B) may be selectively decreased and/or the flow rate QG in the guard line(s) 524 from guard zone(s) 604 (see FIGS. 6A-6B) may be increased to allow less fluid to be drawn into the sample line 528 via sample zone 606 (see FIGS. 6A-6B). When focused sampling system 518 includes a single pump 534, a restrictor valve 526 and/or diameter of sample line 528 and/or guard line(s) 524 may be selected to provide the desired ratio QG/Qs of fluid flow rate in the guard zone(s) 604 (see FIGS. 6A-6B) to the fluid flow rate in the sample zone 606 (see FIGS. 6A-6B).

The flow rate may be altered to affect the flow of fluid and optimize the intake of water or fluid 206 into the sampling system 518. Various devices may be used to measure and adjust the rates to optimize the fluid flow. Initially, it may be desirable to have increased flow into the guard zone(s) 604 (see FIGS. 6A-6B) when the amount of contaminated fluid is high and adjust the flow rate to increase the flow into the sample zone 606 (see FIGS. 6A-6B) once the amount of water or fluid 206 entering the sample zone 606 (see FIGS. 6A-6B) increases. In this manner, the fluid sampling may be manipulated to increase the efficiency of the sampling process and the quality of the sample with which the one or more sample chambers 538 may be filled and/or the quality of a sample analyzed via the one or more sensors S.

Figure 6A:
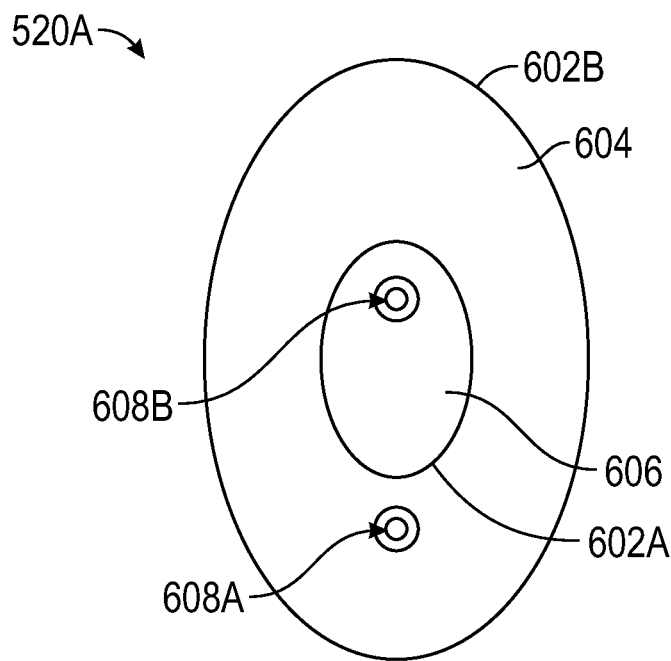
FIGS. 6A-6B are schematic illustrations of an end view of a focused sampling probe according to FIB. 5, as disclosed herein.
Figure 6B:
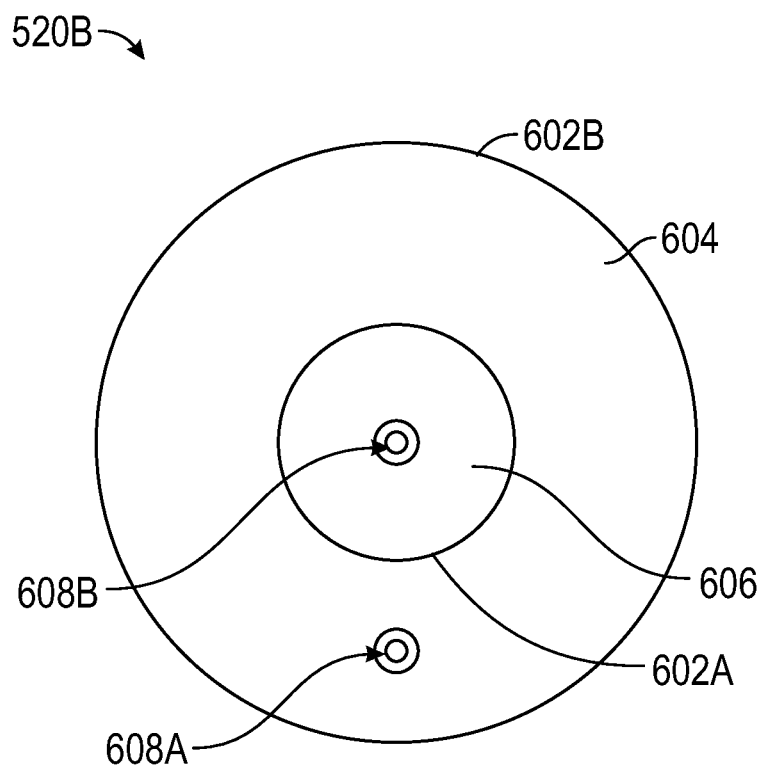

The guard zone 604 (see FIGS. 6A-6B) may be positioned at least partially concentrically about the sample zone 606 (see FIGS. 6A-6B). The sample zone 606 (see FIGS. 6A-6B) and the guard zone 604 (see FIGS. 6A-6B) may be prolate (e.g., oval) or circular in cross section. For example, referring to FIG. 6A, a schematic end view of a focused sampling probe 340A, focused sampling probe 520A includes an inner concentric ring 602A and an outer concentric ring 602B that may define sample zone 604 (e.g., within inner concentric ring 602A) and guard zone 606 (e.g., between inner concentric ring 602A and outer concentric ring 602B). In Inner concentric ring 602A and outer concentric ring 602B may be oval in cross-section shape, thus defining a guard zone 604 having an oval cross section and a sample zone 606 having an oval cross section. One or more sample zone fluid inlets 6087B may be fluidly connected with sample line inlet 528A of sample line 528 and one or more guard zone fluid inlets 608A may be fluidly connected with guard line inlet(s) 524A of sample line 528. A sample zone fluid inlet 608B may be positioned within sample zone 606 such that a distance may be maximized between sample zone fluid inlet 608B and one or more guard zone fluid inlets 608A. FIG. 6B is a schematic end view of a focused sampling probe 520B. Inner concentric ring 602A and outer concentric ring 602B may be circular, or substantially round, in cross section shape, thus defining a guard zone 604 having a circular cross section and a sample zone 606 having a circular cross section. One or more sample zone fluid inlets 608B may be fluidly connected with sample line inlet 528A of sample line 528. A sample zone fluid inlet 608B may be positioned at a center of sample zone 606 and one or more guard zone fluid inlets 608A may be positioned about 10% to about 90% of the radial distance between inner concentric ring 602A and outer concentric ring 602B from inner concentric ring 602A. Alternatively, the sample zone fluid inlet 608B may be positioned at a center of sample zone 606 and one or more guard zone fluid inlets 608A may be positioned about 10% to about 90%, about 15% to about 85%, about 20% to about 80%, about 25% to about 75%, about 30% to about 70%, about 35% to about 65%, or about 40% to about 60% of the radial distance between inner concentric ring 602A and outer concentric ring 602B from inner concentric ring 602A. Oval focused sampling probe 520A or FIG. 6A or round focused sampling probe 520B of FIG. 6B may be utilized in the focused sampling system of 518 of FIG. 5, the focused sampling system 518C of FIG. 9, the focused sampling system of 518D of FIG. 10, or the focused sampling system of 518E of FIG. 11.

As noted hereinabove, a focused sampling system 518 may include one or more MEMS devices 200 and/or one or more sample chambers 538. For example, focused sampling system 518 of FIG. 5 may include MEMS device 200 and first sample chamber 538A, second sample chamber 538B, third sample chamber 538C, fourth sample chamber 538D, and fifth sample chamber 538E. Valves (not shown in FIG. 5) may be utilized to direct the flow of fluid from pump outlet line 534B into discharge line 532 during a pre-sampling time period, including during a flushing time period, and to direct the flow of fluid from pump outlet line 534 into the MEMS device 200 and/or the one or more sample chambers 538 during a sampling time period. It should be noted that a focused sampling system absent any sample chambers 538 may be operable to determine properties of the clean sample line 528 water or fluid without actually taking a sample thereof into a sample chamber 538. In some examples, testing may be automated. In other examples, samples may be tested in a laboratory with a manual operational method of introducing a sample. However, the analysis process may be automated, even in laboratory testing. In essence, sampling may be manual, partially automated, or completely automated with the use of a computer system and other technology, further discussed below.

Figure 7:
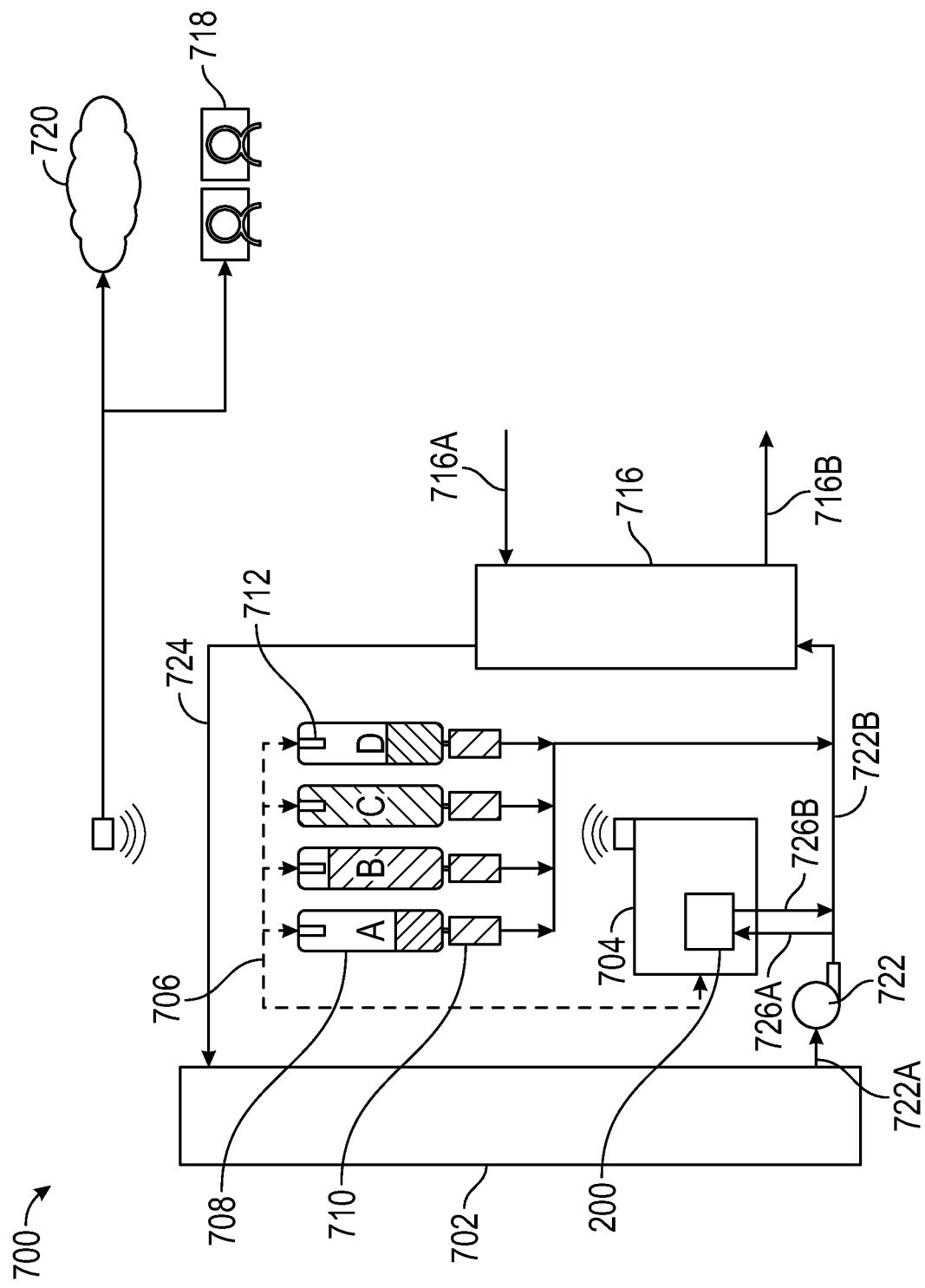
FIG. 7 is a schematic illustration of a MEMS in industrial water operations, as disclosed herein.

Referring now to FIG. 7, wherein FIG. 7 is a schematic illustration of a MEMS in industrial water operation 700, according to some examples disclosed herein. Industrial water operation 700 comprises cooling tower 702; MPS-based chemical water treatment analysis unit 704; fluid level control communications 706; treatment chemical dosing reservoirs 708; which comprises 708A, 708B, 708C, and 708D; metering pumps 710; MEMS 200; level sensor 712, which comprises 712A, 712B, 712C, and 712D; communications link to cloud and control center 714; process fluid inlet and outlet 716A, 716B; control room 718; and cloud 720.

As depicted in FIG. 7, heat exchanger 716 exit line 724 is feed line/inlet to cooling tower 702, whereas cooling tower exit line/outlet 722A is inlet to pump 722, wherein pump 722 outlet 722B feeds into heat exchanger 716, where the process water or fluid 206 may be combined with the freshwater feed 716A of heat exchanger 716. The process stream of pump 722 exit 722B may connect to MPS-based chemical water treatment analysis unit 704 through inlet line 726A and outlet line 726B, wherein MPS-based chemical water treatment analysis unit 704 comprises MEMS sensor device 200. A plurality of parameters may be detected and analyzed by MPS-based chemical water treatment analysis unit 704. For example, corrosion by-products may be detected and the chemical treatment concentration in the process water or fluid stream may be analyzed. Process water or fluid 206 may contact enter MPS-based chemical water treatment analysis unity 704 via inlet 726A and contact at least a portion of the array of MPS sensors 100. Process water or fluid may exit MPS-based chemical water treatment analysis unit 704 via exit line 726B, emptying into pump 722 exit line 722B. Process water or fluid 206 contacting at least a portion of the array of MPS sensors 100 may be analyzed for specific component, as the process water or fluid contacts microcantilever 300. The data generated by MEMS 200 may be transmitted to cloud 720, where the data may be saved and downloaded to control room 718, wherein an analysis may be performed for the purpose of determining the proper dosing requirements for chemical treatment.

In addition to the determination of the proper dosing requirements for chemical treatment, the industrial water operation 100 may be continually monitored, controlled, and adjusted by the control room 718 based on cloud 720 communication between the MPS-based chemical water treatment analysis unit and the control room. The analysis, monitoring, controlling and adjusted may be accomplished in real-time. Consequently, chemical treatment reservoirs 708A, 708B, 708C, 708D may be controlled by control room 718 via cloud communication link 714 or it may be manually controlled at the source (not shown). Metering pumps 710 may dispense the specific amount of dosing of each of chemical treatment reservoirs 708A, 708B 708C, 708D into pump 722 exit line 722B, wherein outlet line 722B is treated water or fluid feed/inlet line to heat exchanger 716. The treated water or fluid may be flushed with fresh water, wherein fresh water may be pumped into heat exchanger 716 via inlet line 716A. The treated water may then be pumped to cooling tower via heat exchanger outlet line 724, wherein line 724 is also the inlet line to cooling tower 702.

Figure 8:
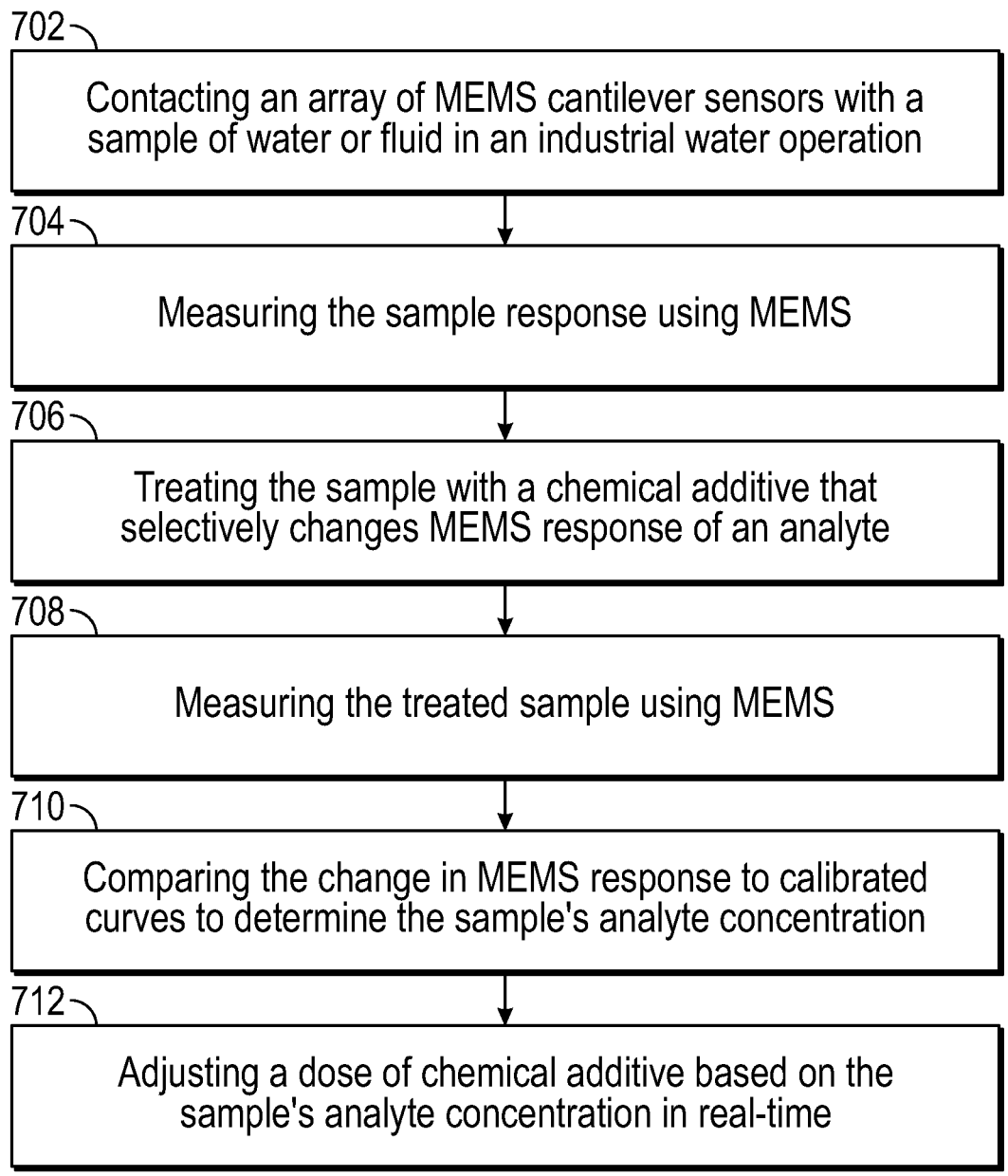
FIG. 8 is a flow chart of a method using MEMS in a general industrial water operation, as disclosed herein.

FIG. 8 is a flow chart depicting a method of analysis, monitoring, and adjusting chemical treatment of an industrial water operation, incorporating MEMS/MPS, according to the present disclosure. The method may comprise: contacting a sample of water of fluid with an array of MEMS/MPS cantilever sensors 702; measuring the sample response using MEMS/MPS 704; treating the sample with a chemical additive that may selectively change the MEMS/MPS response of an analyte 706; measuring the treated sample using MEMS/MPS 708; comparing the change in MEMS/MPS response to calibrated curves to determine the sample's analyte concentration 710; and adjusting a dose of chemical additive based on the sample's analyte concentration in real-time 712.

Alternatively, FIG. 8 depicts a method of dosing one or more components to provide water or fluid 224 having a desired composition for introduction into an industrial water operation 218 (step 712). The method may comprise determining a concentration of the one or more components of the water or fluid 224 in one or more samples 224A of the fluid 224 (steps 702, 704, 706, 708, 710); and adjusting or maintaining the dosing of one or more components of a treatment fluid 229 being introduced into industrial water operation 218 based on the determining of the concentration of the one or more components in the one or more samples 224A of the water or fluid 224 (step 712). The determining of the concentration of the one or more components includes, for each of the one or more samples 224A, contacting the sample 224A of the water or fluid 224 with a MEMS device 200 to provide a sample response indicative of the concentration of the one or more components (steps 702, 704, 706).

The method may further include monitoring a trend in the determined concentration of one or more components of the water or fluid 224 and utilizing the monitoring of the trend in the adjusting or maintaining of the operational parameter of the industrial water operation. Monitoring of trends may be utilized to manage the industrial water operation 218, such as adjusting the composition and flow rate of treatment fluid 229 being introduced into industrial water operation 218; and/or adjusting another operational parameter of the industrial water operation 218. Hence, utilization of MEMS device 200 may provide advance warning and effecting of responsive action prior to the sampling.

Also disclosed herein is a system for servicing an industrial water operation 218. The system may comprise at least one MEMS 200 operable for determining a concentration of one or more components of water or fluid 224 via a sample response indicative of the concentration of the one or more components, wherein the sample response may be obtained via contact of a sample 224A of the water or fluid 224 with the MEMS device 200; and a feedback system (e.g., MPS-based chemical water treatment analysis unit 704, dosing unit fluid level and control communications 706, cloud 720, control room 718, and cloud and control room communication link 714) operable to adjust or maintain one or more operating parameters of the servicing of the industrial water operation based on the determined concentration of the one or more components. The system may provide real-time monitoring and determination of concentration of one or more components of the water or fluid 224.

The systems, methods, and compositions may include any of the various features disclosed herein, including one or more of the following statements.

Statement 1. A method may comprise determining a concentration of one or more components of a fluid in an industrial water operation in real time, wherein the determining of the concentration of the one or more components comprises contacting an array of sensors of a microelectromechanical system (MEMS) device with a sample of the fluid to provide a sample response indicative of the concentration of the one or more components; and adjusting or maintaining at least one operating parameter of the industrial water operation based on the concentration of the one or more components of the fluid.

Statement 2. The method of statement 1, wherein the array of sensors comprises microcantilever-based self-sensing array (SSA) technology.

Statement 3. The method of statement 1 or 2, wherein the array of sensors comprises one or more microcantilever elements, wherein the microcantilever elements comprise a polymer coating, a metal/piezoelectric sandwich, and a silicon coating with a piezoresistive heater.

Statement 4. The method of any of the preceding statements, wherein the array of sensors includes, for each of the one or more components, one or more microcantilever elements comprising a coating sensitive to an analyte specific to each of the one or more components.

Statement 5. The method of any of the preceding statements, wherein the array of sensors includes one or more microcantilever elements comprising a coating sensitive to an analyte specific to each of the one or more components, wherein at least a portion of the coating comprises a polymer.

Statement 6. The method of any of the preceding statements, wherein the array of sensors comprises microcantilevers with integrated piezoelectric sensing elements that provide electrical actuation and sensing of resonance frequency.

Statement 7. The method of any of the preceding statements, wherein the at least one operating parameter comprises corrosion rate, scaling rate, deposition rate, heat transfer rate, cooling tower efficiency, chemical concentration, cycle of concentration, suspended solids measurement, dissolved solids measurement, microbiological activity rate, chemical activity rate, a process performance parameter, a product performance parameter, multiples thereof, combinations thereof, and multiples and combinations thereof.

Statement 8. The method of any of the preceding statements, wherein the MEMS has an operating temperature of about −40° C. to about 70° C.

Statement 9. The method of any of the preceding statements, wherein the adjusting or maintaining at least one operating parameter comprises treating the sample with a chemical additive, wherein the chemical additive changes the MEMS response to a specific analyte, wherein the chemical additive is an acid, base, enzyme, oxidizer, or combination thereof.

Statement 10. The method of statement 9, wherein the chemical additive is selected from the group consisting of orthophosphate, dispersant polymers, azole, phosphonobutanetricarboxylic acid and salts thereof, phosphinosuccinic oligomer, and combinations thereof.

Statement 11. The method of statement 9 or 10, further comprising measuring the treated sample and comparing the change in MEMS response to a calibrated curve.

Statement 12. A method may comprise determining a concentration of one or more components of a fluid in an industrial water operation, wherein the determining of the concentration of the one or more components comprises contacting an array of sensors of a microelectromechanical system (MEMS) device with a sample of the fluid to provide a sample response indicative of the concentration of the one or more components, wherein the array of sensors comprises, for each of the one or more components, one or more microcantilever elements comprises a coating sensitive to an analyte specific to each of the one or more components; and adjusting or maintaining at least one operating parameter of the industrial water operation based on the determining of the concentration of the one or more components of the water or fluid, wherein the adjusting or maintaining the at least one operating parameter comprises treating the sample with a chemical additive, wherein the chemical additive changes the MEMS response to the specific analyte, measuring the treated sample, and comparing the change in the MEMS response to a calibrated curve.

Statement 13. The method of statement 12, wherein the microcantilever elements comprise integrated piezoelectric sensing elements that provide electrical actuation and sensing of resonance frequency.

Statement 14. The method of statement 12 or 13, wherein the microcantilever elements comprise self-sensing array (SSA) technology, and wherein the microcantilever elements comprise a polymer coating, a metal/piezoelectric sandwich, and a silicon coating with a piezoresistive heater.

Statement 15. The method of statement 12, 13, or 14, wherein the chemical additive is selected from the group consisting of orthophosphate, dispersant polymers, azole, phosphonobutanetricarboxylic acid and salts thereof, phosphinosuccinic oligomer, and combinations thereof.

Statement 16. The method of statement 12, 13, 14, or 15, wherein the at least one operating parameter comprises corrosion rate, scaling rate, deposition rate, heat transfer rate, cooling tower efficiency, chemical concentration, cycle of concentration, suspended solids measurement, dissolved solids measurement, microbiological activity rate, chemical activity rate, a process performance parameter, a product performance parameter, multiples thereof, combinations thereof, and multiples and combinations thereof.

Statement 17. The method of statement 12, 13, 14, 15, or 16, wherein the MEMS has an operating temperature of about −40° C. to about 70° C.

Statement 18. A system may comprise at least one microelectromechanical system (MEMS) device comprising an array of sensors comprising one or more microcantilever elements comprising a polymer coating, a metal/piezoelectric sandwich, and a silicon coating with a piezoresistive heater, wherein the MEMS is operable for determining a concentration of one or more components of water or fluid in an industrial water operation via a sample response indicative of the concentration of the one or more components; and a feedback system operable to adjust or maintain one or more operating parameters of the industrial water operation based on the determined concentration of the one or more components of the water or fluid.

Statement 19. The system of statement 18, wherein the feedback system comprises dosing unit fluid level and control communications and a cloud and control room communications link.

Statement 20. The system of statement 18 or 19, wherein the MEMS has an operating temperature of about −40° C. to about 70° C.

To facilitate a better understanding of the present disclosure, the following examples of some of the preferred examples are given. In no way should such examples be read to limit, or to define, the scope of the disclosure.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

Therefore, the present disclosure is well adapted to attain the ends and advantages mentioned as well as those that are inherent therein. The examples disclosed above are illustrative only, as the present embodiments may be modified and practiced in different but equivalent manners apparent to those skilled in the art having the benefit of the teachings herein. Although individual examples are discussed, the present disclosure covers all combinations of all those examples. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the illustrative examples disclosed above may be altered or modified and all such variations are considered within the scope and spirit of the present disclosure. If there is any conflict in the usages of a word or term in this specification and one or more patent(s) or other documents that may be incorporated herein by reference, the definitions that are consistent with this specification should be adopted.

What is claimed is:

1. A method comprising:
    determining a concentration of one or more components of a fluid in an industrial water operation in substantially real time, wherein the determining of the concentration of the one or more components comprises contacting an array of sensors of a microelectromechanical system (MEMS) device with a sample of the fluid to provide a sample response indicative of the concentration of the one or more components;
    adjusting or maintaining, via treatment chemical dosing reservoirs, at least one operating parameter of the industrial water operation based on the concentration of the one or more components of the fluid; and
    circulating treated water through a heat exchanger and back to the MEMS device.

2. The method of claim 1, wherein the array of sensors comprises microcantilever-based self-sensing array (SSA) technology.

3. The method of claim 1, wherein the array of sensors comprises one or more microcantilever elements, wherein the microcantilever elements comprise a polymer coating, a metal/piezoelectric sandwich, and a silicon coating with a piezoresistive heater.

4. The method of claim 1, wherein the array of sensors comprises, for each of the one or more components, one or more microcantilever elements comprising a coating sensitive to an analyte specific to each of the one or more components.

5. The method of claim 1, wherein the array of sensors comprises one or more microcantilever elements comprising a coating sensitive to an analyte specific to each of the one or more components, wherein at least a portion of the coating comprises a polymer.

6. The method of claim 1, wherein the array of sensors comprises microcantilevers with integrated piezoelectric sensing elements that provide electrical actuation and sensing of resonance frequency.

7. The method of claim 1, wherein the adjusting or maintaining at least one operating parameter comprises treating the sample with a chemical additive, wherein the chemical additive changes the MEMS response to a specific analyte, wherein the chemical additive is an acid, base, enzyme, oxidizer, or combination thereof.

8. The method of claim 7, wherein the chemical additive is selected from the group consisting of orthophosphate, dispersant polymers, azole, phosphonobutanetricarboxylic acid and salts thereof, phosphinosuccinic oligomer, and combinations thereof.

9. The method of claim 7, further comprising measuring the treated sample and comparing the change in MEMS response to a calibrated curve.

10. The method of claim 1, wherein the at least one operating parameter comprises corrosion rate, scaling rate, deposition rate, heat transfer rate, cooling tower efficiency, chemical concentration, cycle of concentration, suspended solids measurement, dissolved solids measurement, microbiological activity rate, chemical activity rate, a process performance parameter, a product performance parameter, multiples thereof, combinations thereof, and multiples and combinations thereof.

11. The method of claim 1, wherein the MEMS has an operating temperature of about −40° C. to about 70° C.

12. A method comprising:
    determining a concentration of one or more components of fluid in an industrial water operation, wherein the determining of the concentration of the one or more components comprises contacting an array of sensors of a microelectromechanical system (MEMS) device with a sample of the fluid to provide a sample response indicative of the concentration of the one or more components, wherein the array of sensors comprises, for each of the one or more components, one or more microcantilever elements comprises a coating sensitive to an analyte specific to each of the one or more components;
    adjusting or maintaining, via treatment chemical dosing reservoirs, at least one operating parameter of the industrial water operation based on the determining of the concentration of the one or more components of the water or fluid, wherein the adjusting or maintaining the at least one operating parameter comprises treating the sample with a chemical additive, wherein the chemical additive changes the MEMS response to the specific analyte, measuring the treated sample, and comparing the change in the MEMS response to a calibrated curve; and
    circulating treated water through a heat exchanger and back to the MEMS device.

13. The method of claim 12, wherein the microcantilever elements comprise integrated piezoelectric sensing elements that provide electrical actuation and sensing of resonance frequency.

14. The method of claim 12, wherein the microcantilever elements comprise self-sensing array (SSA) technology, and wherein the microcantilever elements comprise a polymer coating, a metal/piezoelectric sandwich, and a silicon coating with a piezoresistive heater.

15. The method of claim 12, wherein the chemical additive is selected from the group consisting of orthophosphate, dispersant polymers, azole, phosphonobutanetricarboxylic acid and salts thereof, phosphinosuccinic oligomer, and combinations thereof.

16. The method of claim 12, wherein the at least one operating parameter comprises corrosion rate, scaling rate, deposition rate, heat transfer rate, cooling tower efficiency, chemical concentration, cycle of concentration, suspended solids measurement, dissolved solids measurement, microbiological activity rate, chemical activity rate, a process performance parameter, a product performance parameter, multiples thereof, combinations thereof, and multiples and combinations thereof.

17. The method of claim 12, wherein the MEMS has an operating temperature of about −40° C. to about 70° C.

18. A system comprising:
at least one microelectromechanical system (MEMS) device comprising an array of sensors comprising one or more microcantilever elements comprising a polymer coating, a metal/piezoelectric sandwich, and a silicon coating with a piezoresistive heater, wherein the MEMS is operable for determining a concentration of one or more components of water or fluid in an industrial water operation via a sample response indicative of the concentration of the one or more components;
a feedback system operable to adjust or maintain, via treatment chemical dosing reservoirs, one or more operating parameters of the industrial water operation based on the determined concentration of the one or more components of the water or fluid; and
a heat exchanger operable to receive treated water and direct the treated water back to the MEMS device.

19. The system of claim 18, wherein the feedback system comprises dosing unit fluid level and control communications and a cloud and control room communications link.

20. The cement system of claim 18, wherein the MEMS has an operating temperature of about −40° C. to about 70° C.

* * * * *

UNITED STATES PATENT AND TRADEMARK OFFICE
CERTIFICATE OF CORRECTION

| | |
|---|---|
| PATENT NO. | : 11,360,014 B1 |
| APPLICATION NO. | : 17/379858 |
| DATED | : June 14, 2022 |
| INVENTOR(S) | : Dale E. Jamison et al. |

It is certified that error appears in the above-identified patent and that said Letters Patent is hereby corrected as shown below:

On the Title Page

Item (73) Assignee, please correct "Multi-Chem Group, LLC" to -- Halliburton Energy Services, Inc. --.

Signed and Sealed this
Sixteenth Day of August, 2022

Katherine Kelly Vidal
*Director of the United States Patent and Trademark Office*